US007369890B2

(12) United States Patent
Lovett

(10) Patent No.: US 7,369,890 B2
(45) Date of Patent: May 6, 2008

(54) TECHNIQUE FOR DISCRIMINATING BETWEEN COORDINATED AND UNCOORDINATED CARDIAC RHYTHMS

(75) Inventor: Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 583 days.

(21) Appl. No.: 10/435,487

(22) Filed: May 9, 2003

(65) Prior Publication Data
US 2004/0073262 A1    Apr. 15, 2004

Related U.S. Application Data

(63) Continuation of application No. 09/705,155, filed on Nov. 2, 2000, now abandoned.

(51) Int. Cl.
*A61B 5/0402* (2006.01)
(52) U.S. Cl. ...................................... 600/515
(58) Field of Classification Search ................ 600/509, 600/515, 516, 518, 519, 522, 373, 374, 393; 607/4, 5, 9, 14, 25, 28, 116, 119, 120, 122, 607/126, 128
See application file for complete search history.

(56) References Cited

U.S. PATENT DOCUMENTS

| 3,692,027 | A | 9/1972 | Ellinwood, Jr. |
| 4,003,379 | A | 1/1977 | Ellinwood, Jr. |
| 4,146,029 | A | 3/1979 | Ellinwood, Jr. |
| 4,202,340 | A | 5/1980 | Langer et al. |
| 4,271,192 | A | 6/1981 | Wurtman et al. |

(Continued)

FOREIGN PATENT DOCUMENTS

EP    0054138 A1    6/1982

(Continued)

OTHER PUBLICATIONS

Pastore, Joseph M., "Method And Apparatus For Detecting Oscillations In Cardiac Rhythm", U.S. Appl. No. 10/172,825, filed Jun. 14, 2002, 33 pages.

(Continued)

*Primary Examiner*—Carl Layno
*Assistant Examiner*—Frances P. Oropeza
(74) *Attorney, Agent, or Firm*—Schwegman, Lundberg & Woessner, P.A.

(57) ABSTRACT

A system and method for discriminating cardiac rhythms in sensed cardiac complexes associated with at least two cardiac signals, which includes at least two electrodes disposed at different locations in a heart for sensing at least two cardiac signals. A controller through a sensing circuit receives the sensed at least two cardiac signals from the electrodes and processes the sensed at least two cardiac signals to compute interelectrode time differences between the cardiac complexes associated with one of the at least two sensed cardiac signals, and corresponding cardiac complexes associated with the other of the at least two sensed cardiac signals. The controller further computes a detection time difference variability from the computed interelectrode detection time difference variabilities. Then the controller compares the computed detection time difference variability to a predetermined detection time difference variability threshold value to discriminate whether the sensed at least two cardiac signals have a coordinated or an uncoordinated cardiac rhythm.

44 Claims, 7 Drawing Sheets

U.S. PATENT DOCUMENTS

| | | |
|---|---|---|
| 4,281,664 A | 8/1981 | Duggan |
| 4,299,220 A | 11/1981 | Dorman |
| 4,470,987 A | 9/1984 | Wurtman et al. |
| 4,544,371 A | 10/1985 | Dormandy, Jr. et al. |
| 4,556,063 A | 12/1985 | Thompson et al. |
| 4,559,946 A | 12/1985 | Mower |
| 4,651,716 A | 3/1987 | Forester et al. |
| 4,674,518 A | 6/1987 | Salo |
| 4,686,987 A | 8/1987 | Salo et al. |
| 4,693,253 A | 9/1987 | Adams |
| 4,787,389 A | 11/1988 | Tarjan |
| 4,790,317 A | 12/1988 | Davies |
| 4,871,351 A | 10/1989 | Feingold |
| 4,880,005 A | 11/1989 | Pless et al. |
| 4,897,987 A | 2/1990 | Spalla |
| 4,904,472 A | 2/1990 | Belardinelli et al. |
| 4,924,875 A | 5/1990 | Chamoun |
| 4,940,054 A | 7/1990 | Grevis et al. |
| 4,944,299 A | 7/1990 | Silvian |
| 4,949,719 A | 8/1990 | Pless et al. |
| 4,980,379 A | 12/1990 | Belardinelli et al. |
| 4,987,897 A | 1/1991 | Funke |
| 5,002,052 A | 3/1991 | Haluska |
| 5,014,698 A | 5/1991 | Cohen |
| 5,040,533 A | 8/1991 | Fearnot |
| 5,041,107 A | 8/1991 | Heil, Jr. |
| 5,042,497 A | 8/1991 | Shapland |
| 5,058,581 A | 10/1991 | Silvian |
| 5,087,243 A | 2/1992 | Avitall |
| 5,113,869 A | 5/1992 | Nappholz et al. |
| 5,127,404 A | 7/1992 | Wyborny et al. |
| 5,137,019 A | 8/1992 | Pederson et al. |
| 5,179,945 A | 1/1993 | Van Hofwegen et al. |
| 5,179,946 A | 1/1993 | Weiss |
| 5,184,614 A | 2/1993 | Collins et al. |
| 5,188,105 A | 2/1993 | Keimel |
| 5,190,035 A | 3/1993 | Salo et al. |
| 5,193,535 A | 3/1993 | Bardy et al. |
| 5,215,083 A | 6/1993 | Drane et al. |
| 5,220,917 A | 6/1993 | Cammilli et al. |
| 5,269,301 A | 12/1993 | Cohen |
| 5,282,836 A | 2/1994 | Kreyenhagen et al. |
| 5,284,136 A | 2/1994 | Hauck et al. |
| 5,292,338 A | 3/1994 | Bardy |
| 5,301,677 A | 4/1994 | Hsung |
| 5,305,745 A | 4/1994 | Zacouto |
| 5,325,856 A | 7/1994 | Nitzsche et al. |
| 5,334,222 A | 8/1994 | Salo et al. |
| 5,342,408 A | 8/1994 | deCoriolis et al. |
| 5,346,506 A | 9/1994 | Mower et al. |
| 5,350,406 A | 9/1994 | Nitzsche et al. |
| 5,353,800 A | 10/1994 | Pohndorf et al. |
| 5,354,317 A | 10/1994 | Alt |
| 5,366,485 A | 11/1994 | Kroll et al. |
| 5,368,028 A | 11/1994 | Palti |
| 5,379,776 A | 1/1995 | Murphy et al. |
| 5,391,190 A | 2/1995 | Pederson et al. |
| 5,404,877 A | 4/1995 | Nolan et al. |
| 5,405,362 A | 4/1995 | Kramer et al. |
| 5,416,695 A | 5/1995 | Stutman et al. |
| 5,417,717 A | 5/1995 | Salo et al. |
| 5,431,682 A | 7/1995 | Hedberg |
| 5,439,483 A | 8/1995 | Duong-Van |
| 5,441,525 A | 8/1995 | Shelton et al. |
| 5,456,692 A | 10/1995 | Smith, Jr. et al. |
| 5,458,619 A | 10/1995 | Olson |
| 5,460,605 A | 10/1995 | Tuttle et al. |
| 5,464,434 A | 11/1995 | Alt |
| 5,476,503 A | 12/1995 | Yang |
| 5,487,752 A | 1/1996 | Salo et al. |
| 5,489,293 A | 2/1996 | Pless et al. |
| 5,496,360 A | 3/1996 | Hoffmann et al. |
| 5,499,971 A | 3/1996 | Shapland et al. |
| 5,500,008 A | 3/1996 | Fain |
| 5,501,701 A | 3/1996 | Markowitz et al. |
| 5,522,853 A | 6/1996 | Kroll |
| 5,540,723 A | 7/1996 | Ideker et al. |
| 5,540,728 A | 7/1996 | Shelton et al. |
| 5,545,186 A * | 8/1996 | Olson et al. .................. 607/14 |
| 5,545,205 A | 8/1996 | Schulte et al. |
| 5,551,953 A | 9/1996 | Lattin et al. |
| 5,556,421 A | 9/1996 | Prutchi et al. |
| 5,562,711 A | 10/1996 | Yerich et al. |
| 5,562,713 A | 10/1996 | Silvian |
| 5,579,876 A | 12/1996 | Adrian et al. |
| 5,584,868 A | 12/1996 | Salo et al. |
| 5,586,556 A | 12/1996 | Spivey et al. |
| 5,591,215 A | 1/1997 | Greenhut et al. |
| 5,603,331 A | 2/1997 | Heemels et al. |
| 5,607,418 A | 3/1997 | Arzbaecher |
| 5,607,463 A | 3/1997 | Schwartz et al. |
| 5,632,766 A | 5/1997 | Hsu |
| 5,634,899 A | 6/1997 | Shapland et al. |
| 5,662,689 A | 9/1997 | Elsberry et al. |
| 5,676,686 A | 10/1997 | Jensen et al. |
| 5,683,424 A | 11/1997 | Brown et al. |
| 5,690,682 A | 11/1997 | Buscemi et al. |
| 5,693,075 A | 12/1997 | Plicchi et al. |
| 5,703,125 A | 12/1997 | Bovy et al. |
| 5,706,829 A | 1/1998 | Kadri |
| 5,709,215 A | 1/1998 | Perttu et al. |
| 5,720,770 A | 2/1998 | Nappholz et al. |
| 5,725,561 A | 3/1998 | Stroebel et al. |
| 5,725,562 A | 3/1998 | Sheldon |
| 5,730,125 A | 3/1998 | Prutchi et al. |
| 5,730,141 A | 3/1998 | Fain et al. |
| 5,733,313 A | 3/1998 | Barreras, Sr. et al. |
| RE35,779 E | 4/1998 | Alferness et al. |
| 5,749,900 A | 5/1998 | Schroeppel et al. |
| 5,772,604 A | 6/1998 | Langberg et al. |
| 5,782,876 A | 7/1998 | Flammang |
| 5,782,879 A | 7/1998 | Rosborough et al. |
| 5,797,967 A | 8/1998 | KenKnight |
| 5,800,464 A | 9/1998 | Kieval |
| 5,800,498 A | 9/1998 | Obino et al. |
| 5,814,081 A | 9/1998 | Ayers et al. |
| 5,814,089 A | 9/1998 | Stokes et al. |
| 5,817,131 A | 10/1998 | Elsberry et al. |
| 5,833,603 A | 11/1998 | Kovacs et al. |
| 5,836,935 A | 11/1998 | Ashton et al. |
| 5,874,420 A | 2/1999 | Pelleg |
| 5,876,353 A | 3/1999 | Riff |
| 5,879,295 A | 3/1999 | Li et al. |
| 5,893,881 A * | 4/1999 | Elsberry et al. ................ 607/5 |
| 5,899,928 A | 5/1999 | Sholder et al. |
| 5,913,879 A | 6/1999 | Ferek-Petric et al. |
| 5,916,239 A | 6/1999 | Geddes et al. |
| 5,919,210 A | 7/1999 | Lurie et al. |
| 5,925,066 A | 7/1999 | Kroll et al. |
| 5,949,659 A | 9/1999 | Lesche |
| 5,954,761 A | 9/1999 | Macheck et al. |
| 5,957,861 A | 9/1999 | Combs et al. |
| 5,957,957 A | 9/1999 | Sheldon |
| 5,967,986 A | 10/1999 | Cimochowski et al. |
| 5,968,079 A | 10/1999 | Warman et al. |
| 5,978,705 A | 11/1999 | KenKnight et al. |
| 5,991,660 A | 11/1999 | Goyal |
| 5,991,668 A | 11/1999 | Leinders et al. |
| 6,016,443 A | 1/2000 | Ekwall et al. |
| 6,016,447 A | 1/2000 | Juran et al. |
| 6,016,448 A | 1/2000 | Busacker et al. |
| 6,022,322 A | 2/2000 | Prutchi |
| 6,035,233 A | 3/2000 | Schroeppel et al. |
| 6,044,297 A | 3/2000 | Sheldon et al. |

| | | |
|---|---|---|
| 6,049,735 A | 4/2000 | Hartley et al. |
| 6,076,015 A | 6/2000 | Hartley et al. |
| 6,078,834 A | 6/2000 | Lurie et al. |
| 6,104,949 A | 8/2000 | Pitts Crick et al. |
| 6,112,116 A | 8/2000 | Fischell et al. |
| 6,112,117 A | 8/2000 | KenKnight et al. |
| 6,115,636 A | 9/2000 | Ryan |
| 6,128,526 A | 10/2000 | Stadler et al. |
| 6,140,740 A | 10/2000 | Porat et al. |
| 6,141,588 A | 10/2000 | Cox et al. |
| 6,154,672 A | 11/2000 | Pendekanti et al. |
| 6,154,675 A | 11/2000 | Juran et al. |
| 6,155,267 A | 12/2000 | Nelson |
| 6,161,042 A | 12/2000 | Hartley et al. |
| 6,168,801 B1 | 1/2001 | Heil, Jr. et al. |
| 6,198,394 B1 | 3/2001 | Jacobsen et al. |
| 6,200,265 B1 | 3/2001 | Walsh et al. |
| 6,203,495 B1 | 3/2001 | Bardy |
| 6,206,914 B1 | 3/2001 | Soykan et al. |
| 6,213,942 B1 | 4/2001 | Flach et al. |
| 6,221,011 B1 | 4/2001 | Bardy |
| 6,231,516 B1 | 5/2001 | Keilman et al. |
| 6,237,398 B1 | 5/2001 | Porat et al. |
| 6,238,367 B1 | 5/2001 | Christiansen et al. |
| 6,251,125 B1 | 6/2001 | KenKnight et al. |
| 6,254,573 B1 | 7/2001 | Haim et al. |
| 6,256,233 B1 | 7/2001 | Glass |
| 6,261,230 B1 | 7/2001 | Bardy |
| 6,264,606 B1 | 7/2001 | Ekwall et al. |
| 6,266,554 B1 * | 7/2001 | Hsu et al. ................... 600/515 |
| 6,270,457 B1 | 8/2001 | Bardy |
| 6,272,377 B1 | 8/2001 | Sweeney et al. |
| 6,277,072 B1 | 8/2001 | Bardy |
| 6,277,078 B1 | 8/2001 | Porat et al. |
| 6,278,894 B1 | 8/2001 | Salo et al. |
| 6,280,380 B1 | 8/2001 | Bardy |
| 6,285,898 B1 | 9/2001 | Ben-Haim |
| 6,298,267 B1 | 10/2001 | Rosborough et al. |
| 6,298,272 B1 | 10/2001 | Peterfeso et al. |
| 6,309,370 B1 | 10/2001 | Haim et al. |
| 6,312,378 B1 | 11/2001 | Bardy |
| 6,317,615 B1 | 11/2001 | KenKnight et al. |
| 6,317,631 B1 | 11/2001 | Ben-Haim et al. |
| 6,331,160 B1 | 12/2001 | Bardy |
| 6,336,903 B1 | 1/2002 | Bardy |
| 6,358,202 B1 | 3/2002 | Arent |
| 6,358,203 B2 | 3/2002 | Bardy |
| 6,361,522 B1 | 3/2002 | Scheiner et al. |
| 6,361,780 B1 | 3/2002 | Ley et al. |
| 6,368,284 B1 | 4/2002 | Bardy |
| 6,370,424 B1 | 4/2002 | Prutchi |
| 6,398,728 B1 | 6/2002 | Bardy |
| 6,411,840 B1 | 6/2002 | Bardy |
| 6,411,844 B1 | 6/2002 | Kroll et al. |
| 6,424,847 B1 | 7/2002 | Mastrototaro et al. |
| 6,438,419 B1 | 8/2002 | Callaway et al. |
| 6,440,066 B1 | 8/2002 | Bardy |
| 6,442,413 B1 | 8/2002 | Silver |
| 6,443,949 B2 | 9/2002 | Altman |
| 6,453,195 B1 | 9/2002 | Thompson |
| 6,459,917 B1 | 10/2002 | Gowda et al. |
| 6,459,929 B1 | 10/2002 | Hopper et al. |
| 6,468,263 B1 | 10/2002 | Fischell et al. |
| 6,473,640 B1 | 10/2002 | Erlebacher |
| 6,478,737 B2 | 11/2002 | Bardy |
| 6,501,983 B1 | 12/2002 | Natarajan et al. |
| 6,511,477 B2 | 1/2003 | Altman et al. |
| 6,518,245 B1 | 2/2003 | Anderson et al. |
| 6,519,488 B2 | 2/2003 | KenKnight et al. |
| 6,539,256 B1 | 3/2003 | KenKnight et al. |
| 6,689,117 B2 | 2/2004 | Sweeney et al. |
| 6,693,133 B1 | 2/2004 | Lopaschuk et al. |
| 6,766,195 B1 * | 7/2004 | Bornzin et al. ............... 607/14 |
| 6,802,811 B1 | 10/2004 | Slepian |
| 6,824,561 B2 | 11/2004 | Soykan et al. |
| 6,839,591 B2 | 1/2005 | KenKnight et al. |
| 7,072,711 B2 | 7/2006 | Girouard et al. |
| 2001/0051787 A1 | 12/2001 | Haller et al. |
| 2002/0026228 A1 | 2/2002 | Schauerte |
| 2002/0045809 A1 | 4/2002 | Ben-Haim |
| 2002/0087116 A1 | 7/2002 | Hartlaub |
| 2002/0099302 A1 | 7/2002 | Bardy |
| 2002/0099328 A1 | 7/2002 | Scheiner et al. |
| 2002/0120306 A1 | 8/2002 | Zhu et al. |
| 2002/0169485 A1 | 11/2002 | Pless et al. |
| 2003/0004403 A1 | 1/2003 | Drinan et al. |
| 2003/0045805 A1 | 3/2003 | Sheldon et al. |
| 2003/0060854 A1 | 3/2003 | Zhu |
| 2003/0069606 A1 | 4/2003 | Girouard et al. |
| 2003/0153952 A1 | 8/2003 | Auricchio et al. |
| 2003/0158584 A1 | 8/2003 | Cates et al. |
| 2003/0208240 A1 | 11/2003 | Pastore et al. |
| 2003/0233132 A1 | 12/2003 | Pastore et al. |
| 2004/0002739 A1 | 1/2004 | Cates et al. |
| 2005/0043675 A1 | 2/2005 | Pastore et al. |
| 2005/0137626 A1 | 6/2005 | Pastore et al. |
| 2005/0288721 A1 | 12/2005 | Girouard et al. |
| 2006/0247686 A1 | 11/2006 | Girouard et al. |

FOREIGN PATENT DOCUMENTS

| | | |
|---|---|---|
| EP | 0347708 A1 | 12/1989 |
| EP | 0467695 A2 | 1/1992 |
| EP | 0545628 A2 | 6/1993 |
| EP | 0550343 A1 | 7/1993 |
| EP | 0550344 A1 | 7/1993 |
| EP | 0620420 A1 | 10/1994 |
| EP | 0674916 A2 | 10/1995 |
| EP | 1050265 A2 | 11/2000 |
| WO | WO-93/20888 A1 | 10/1993 |
| WO | WO-96/32984 A1 | 10/1996 |
| WO | WO-97/06854 A1 | 2/1997 |
| WO | WO-97/25098 A1 | 7/1997 |
| WO | WO-97/33513 A1 | 9/1997 |
| WO | WO-98/34537 A1 | 8/1998 |
| WO | WO-00/04947 A2 | 2/2000 |
| WO | WO-00/07497 A1 | 2/2000 |
| WO | WO-01/08748 A1 | 2/2001 |
| WO | WO-01/30436 A2 | 5/2001 |

OTHER PUBLICATIONS

"PCT International Search Report", for International Application No. PCT/US 03/36364, dated Apr. 16, 2004,5 pages.

Arnaud, Claire , et al., "iNOS is a mediator of the heat stress-induced preconditioning against myocardial infarction in vivo in the rat", *Cardiovascular Research*, 58, (2003),118-125.

Bralet, J , et al., "Vasopeptidase inhibitors: an emerging class of cardiovascular drugs", *Trends Pharmacol Sci.*, 22(3), (Mar. 2001),106-9.

Brunner, Friedrich , "Attenuation of myocardial ischemia/reperfusion injury in mice with myocyte-specific overexpression of endothelial nitric oxide synthase", *Cardiovascular Research*, 57, (2003),55-62.

Burns, Brent E., "Fabrication Technology for a Chronic In-Vivo Pressure Sensor", *1984 International Electron Devices Meeting Technical Digest*, (1984),210-212.

Carr, William N., "Integrated Pressure Sensor With Remote Power Source and Remote Readout", *The 8th International Conference on Solid-State Sensors and Actuators and Eurosensors IX, Digest of Technical Papers*, Stockholm, Sweden, (Jun. 25-29, 1995),624-627.

Chau, Hin-Leung , "An Ultraminiature Solid-State Pressure Sensor for a Cardiovascular Catheter", *IEEE Transactions on Electron Devices*, (Dec. 1988),2355-2362.

Colonna, P , "Myocardial infarction and left ventricular remodeling: results of the CEDIM trial", *Am Heart J.*, (Feb. 2000, 139(2 Pt 3)),S124-30.

Ferdinandy, Peter, et al., "Nitric oxide, superoxide, and peroxynitrite in myocardial ischaemia-reperfusion injury and preconditioning", *British Journal of Pharmacology*, 138(4), (2003),532-543.

Flögel, Ulrich, "Myoglobin: A scanvenger of bioactive NO", *PNAS*, 98(2), (Jan. 16, 2001),735-740.

Gewaltig, Michael T., "Vasoprotection by nitric oxide: mechanisms and therapeutic potential", *Cardiovascular Research*, 55, (Feb. 14, 2002),250-260.

Girouard, S. D., "Method and Apparatus to Modulate Cellular Regeneration Post Myocardial Infarct", U.S. Appl. No. 10/862,716, filed Jun. 7, 2004, 71 Pages.

Hada, Yoshiyuki, et al., "Pulsus alternans determined by biventricular simultaneous systolic time intervals", *Circulation*, 65(3), (Mar. 1982),617-26.

Hsia, Peng W., et al., "Absolute Depolarization Vector Characteristics Associated with Successful Defibrillation: Evidence of a Vulnerable Period During Ventricular Fibrillation", *Circulation*, 82 (4), *Supplement III, Abstracts*, Abstract No. 2933,(Oct. 1990),III-738.

Hsia, Peng W., et al., "Genesis of Slgmoidal Dose-Response Curve During Defibrillation by Random Shock: A Theoretical Model Based on Experimental Evidence for a Vulnerable Window During Ventricular Fibrillation", *Pace*, 13, NASPE Young Investigator Awardee-1990,(Oct. 1990),pp. 1326-1342.

Hsia, Peng W., et al., "Improved Nonthoracotmy Defibrillation Based on Ventricular Fibrillation Waveform Characteristics", *PACE, 18—NASPE Abstracts*, Abstract No. 29,(Apr. 1995),p. 803.

Hsu, William, et al., "Effect of Shock Timing on Defibrillation Success", *Pace*, 20, Part II,(1997),pp. 153-157.

Jones, Douglas L., et al., "Ventricular Fibrillation: The Importance of Being Coarse?", *Journal of Electrocardiology*, 17 (4), (1984),pp. 393-399.

Konta, Tsuyoshi, et al., "Significance of Discordant ST Alternans in Ventricular Fibrillation", *Circulation*, 82(6), (Dec. 1990),2185-2189.

Kuelz, Kathy W., et al., "Integration of Absolute Ventricular Fibrillation Voltage Correlates with Successful Defibrillation", *IEEE Transactions on Biomedical Engineering*, 41 (8), (Aug. 1994),pp. 782-791.

Lee, Y. C., et al., "Pulsus alternans in patients with congestive cardiomyopathy", *Circulation*, 65(7), (Jun. 1982),1533-4.

Lehman, J, et al., "Gene regulatory mechanisms governing energy metabolism during cardiac hypertrophic growth", *Heart Fail Rev.*, (Apr. 2000),175-85.

Levin, L, "Researchers present findings at European cardiology conference", *Advisory Board Daily Briefing, 8. Clinical Outlook*, (Sep. 2002),8 pages [see pp. 5,6].

Li, Qianghong, "Gene Therapy With Inducible Nitric Oxide Synthase Protects Against Myocardial Infarction via a Cyclooxygenase-2-Dependent Mechanism", *Circulation Research*, 92, (2003),741-748.

Lopaschuk, G., "Metabolic abnormalities in the diabetic heart", *Heart Failure Reviews*, (Apr. 2002),149-59.

Luepker, R. V., et al., "Transthoracic Electrical Impedance: Quantitative Evaluation of a Non-Invasive Measure of Thoracic Fluid Volume", *American Heart Journal*, 85(1), (Jan. 1973),83-93.

Mai, J., et al., "Enhanced Rate Response Algorithm for Orthostatic Compensation Pacing", *Pacing Clin Electrophysiol. (PACE) Abstracts*, 23 (Pt 2), (Apr. 2000),722.

Min, Mart, et al., "Electrical Impedance and Cardiac Monitoring-Technology, Potential and Applications", *International Journal of Bioelectromagnetism*, 5, (2003),53-56.

Mower, Morton M., et al., "Synchronization of Low-Energy Pulses to Rapid Deflection Signals as a Possible Mechanism of Subthreshold Ventricular Defibrillation", *Abstracts of the 55th Scientific Sessions*, Abstract No. 298,(1982),p. II-75.

Ostadal, Petr, et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003),45-50.

Paolocci, Nazareno, et al., "Positive inotropic and lusitropic effects of HNO/NO- in failing hearts: Independence from beta-adrenergic signaling", *PNAS*, vol. 100, No. 9, (Apr. 29, 2003),5537-5542.

Pastore, Joseph M., "Drug Delivery System and Method Employing External Drug Delivery Device in Conjuction With Computer Network", U.S. Appl. No. 10/742,574, filed Dec. 19, 2003, 36 pages.

Pastore, Joseph M., "Method And Apparatus For Modulating Cellular Metabolism During Post-Ischemia Or Heart Failure", U.S. Appl. No. 10/645,823, filed Aug. 21, 2003, 46 pages.

Rizos, I, "Three-year survival of patients with heart failure caused by dilated cardiomyopathy and L-carnitine administration", *Am Heart J.*, 139(2 Pt 3), (Feb. 2000),Am Heart J.

Rosborough, John P., et al., "Electrical Therapy for Pulseless Electrical Activity", *NASPE*, 23(4), Part II, Abstract,(Apr. 2000),591.

Rubenstein, Donald S., et al., "Premature Beats Elicit a Phase Reversal of Mechanoelectrical Alternans in Cat Ventricular Myocytes", *Circulation*, vol. 91, No. 1, Jan. 1995, American Heart Association,(Jan. 1, 1995),201-214.

Sabbah, H, et al., "Partial fatty acid oxidation inhibitors: a potentially new class of drugs for heart failure", *Eur J Heart Fail.*, 4(1), (Jan. 2002),3-6.

Salloum, Fadi, "Sildenafil Induces Delayed Preconditioning Through Inducible Nitric Oxide Synthase-Dependent Pathway in Mouse Heart", *Circulation Research*, 92, (Apr. 4, 2003),595-597.

Schaefer, Saul, et al., "Clinical and hemodynamic characteristics of patients with inducible pulsus alternans", *American Heart Journal*, vol. 115, No. 6, (Jun. 1988),1251-7.

Smith, Damon, et al., "Influence of the Aortic Component of the Second Heart Sound on Left Ventricular Maximal Negative dP/dt in the Dog", *Am. J. Cardiol.*, 55: 205, (1985),205-209.

Spiegel, Egbert, "A CMOS Sensor and Signal Conversion Chip for Monitoring Arterial Blood Pressure and Temperature", *IEEE International Solid-State Circuits Conference.*, (Feb. 20, 1992),126-127.

Stanley, W, et al., "Energy metabolism in the normal and failing heart: potential for therapeutic interventions", *Heart Fail Rev.*, (Apr. 2002),115-30.

Stanley, W, "Partial fatty acid oxidation inhibitors for stable angina", *Expert Opin Investig Drugs*, 11(5), (May 2002),615-29.

Suematsu, Yoshihiro, et al., "L-Arginine given after ischaemic preconditioning can enhance cardioprotection in isolated rat hearts", *European Journal of Cardio-thoracic Surgery*, 19, (2001),873-879.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolff, A, et al., "Metabolic approaches to the treatment of ischemic heart disease: the clinicians' perspective", *Heart Fail Rev.*, (Apr. 2002),187-203.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41, No. 3, (Mar. 2003),474-480.

Wunderlich, Carsten, "Acute Inhibition of Myoglobin Impairs Contractility and Energy State of iNOS-Overexpressing Hearts", *Circulation Research*, 92, (2003),1352-1358.

Wynn, R, "Cardiovascular drugs and dental considerations", *Cardiovascular drugs and dental considerations, J Calif Dent Assoc.*, 28(7), (Jul. 2000),9-26.

Ziaie, Babak, "A Single-Channel Implantable Microstimulator for Functional Neuromuscular Stimulation", *IEEE Transactions on Biomedical Engineering*, 44, (Oct. 1997),909-920.

"U.S. Appl. No. 09/705,155 Advisory Action mailed May 2, 2003", 3 pgs.

"U.S. Appl. No. 09/705,155 Final Office Action mailed Jan. 9, 2003", 6 pgs.

"U.S. Appl. No. 09/705,155 Non Final Office Action mailed Jun. 28, 2002", 8 pgs.

"U.S. Appl. No. 09/705,155 Response filed Apr. 9, 2003 to Final Office Action mailed Jan. 9, 2003", 15 pgs.

"U.S. Appl. No. 09/705,155 Response filed Oct. 28, 2002 to Non Final Office Action mailed Jun. 28, 2002", 9 pgs.

"U.S. Appl. No. 10/293,907 Non Final Office Action mailed Aug. 11, 2005", 28 pgs.

"U.S. Appl. No. 10/293,907 Notice of Allowance mailed Feb. 13, 2006", 6 pgs.

"U.S. Appl. No. 10/293,907 Response filed Nov. 14, 2005 to Non Final Office Action mailed Aug. 11, 2005", 10 pgs.

"U.S. Appl. No. 10/396,946 Non Final Office Action mailed Jul. 16, 2003", 11 pgs.

"U.S. Appl. No. 10/396,946 Non Final Office Action mailed Dec. 19, 2003", 7 pgs.

"U.S. Appl. No. 10/396,946 Notice of Allowance mailed Aug. 26, 2004", 6 pgs.

"U.S. Appl. No. 10/396,946 Response filed May 19, 2004 to Non Final Office Action mailed Dec. 19, 2003", 6 pgs.

"U.S. Appl. No. 10/396,946 Response filed Oct. 16, 2003 to Non Final Office Action mailed Jul. 16, 2003", 9 pgs.

"U.S. Appl. No. 10/645,823 Non Final Office Action mailed Mar. 8, 2007", 8 pgs.

"U.S. Appl. No. 10/645,823 Notice of Allowance mailed Aug. 27, 2007", 7 pgs.

"U.S. Appl. No. 10/645,823 Response filed Jun. 8, 2007 to Non Final Office Action mailed Mar. 8, 2007", 19 pgs.

"U.S. Appl. No. 10/742,574, Response filed Sep. 25, 2007 to Final Office Action mailed Aug. 7, 2007", 17 pgs.

"U.S. Appl. No. 10/742,574 Supplemental Amendment & Response filed Jan. 24, 2007 to Final Office Action Mailed Oct. 27, 2006 and Advisory Action dated Dec. 21, 2006", 17 Pages.

"U.S. Appl. No. 10/742,574 Advisory Action mailed Dec. 21, 2006", 3 pgs.

"U.S. Appl. No. 10/742,574 Final Office Action mailed Aug. 7, 2007", 12 pgs.

"U.S. Appl. No. 10/742,574 Final Office Action mailed Oct. 27, 2006", 14 pgs.

"U.S. Appl. No. 10/742,574 Non Final Office Action mailed Feb. 12, 2007", 13 pgs.

"U.S. Appl. No. 10/742,574 Non Final Office Action mailed May 23, 2006", 11 pgs.

"U.S. Appl. No. 10/742,574 Response filed May 14, 2007 to Non Final Office Action mailed Feb. 12, 2007", 15 pgs.

"U.S. Appl. No. 10/742,574 Response filed Aug. 23, 2006 to Non Final Office Action mailed May 23, 2006", 17 pgs.

"U.S. Appl. No. 10/742,574 Response filed Dec. 7, 2006 to Final Office Action mailed Oct. 27, 2006", 16 pgs.

"U.S. Appl. No. 10/922,650 Final Office Action mailed Apr. 11, 2007", 11 pgs.

"U.S. Appl. No. 10/922,650 Non Final Office Action filed Jun. 20, 2007", 10 pgs.

"U.S. Appl. No. 10/922,650 Non Final Office Action mailed Sep. 27, 2006", 9 pgs.

"U.S. Appl. No. 10/922,650 Response filed Jan. 25, 2007 to Non Final Office Action mailed Sep. 27, 2006", 15 pgs.

"U.S. Appl. No. 10/922,650 Response filed Jun. 11, 2007 to Final Office Action mailed Apr. 11, 2007", 15 pgs.

"U.S. Appl. No. 10/922,650 Response filed Sep. 19, 2007 to Non Final Office Action mailed Jun. 20, 2007", 17 pgs.

* cited by examiner

TECHNIQUE FOR DISCRIMINATING BETWEEN COORDINATED AND UNCOORDINATED CARDIAC RHYTHMS

CROSS-REFERENCE TO RELATED APPLICATION(S)

This application is a continuation of U.S. patent application Ser. No. 09/705,155, filed on Nov. 2, 2000, now abandoned the specification of which is incorporated herein by reference.

TECHNICAL FIELD

The present invention relates generally to the field of medical devices, and more particularly, it pertains to cardiac rhythm management systems capable of discriminating between coordinated and uncoordinated cardiac rhythms.

BACKGROUND

When functioning properly, the human heart maintains its own intrinsic rhythm, and is capable of pumping adequate blood throughout the body's circulatory system. The body's autonomic nervous system regulates intrinsic electrical heart activity signals that are conducted to atrial and ventricular heart chambers on the left and right sides of the heart. The electrical heart activity signals trigger resulting heart contractions that pump blood. However, some people have irregular and uncoordinated cardiac rhythms, referred to as arrhythmias. Some of the most common arrhythmias are atrial fibrillation (AF) and atrial flutter (AFL). Atrial fibrillation can result in significant patient discomfort and even death because of a number of associated problems, including: (1) an irregular heart rate which causes the patient discomfort and anxiety, (2) loss of synchronous atrioventricular contractions which interferes with cardiac hemodynamics, resulting in varying levels of congestive heart failure, and (3) stasis of blood flow, which increases the vulnerability to thromboembolism.

One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such a system may be implanted in a patient to deliver therapy to the heart.

Cardiac rhythm management systems include, among other things, implanted rhythm management devices. Implanted rhythm management devices deliver, among other things, timed sequences of low-energy electrical stimuli, called pace pulses, to the heart, such as via a transvenous lead wire or catheter (referred to as a "lead") having one or more electrodes disposed in or about the heart. Coordinated heart contractions can be initiated in response to such pace pulses (this is referred to as "capturing" the paced heart). By properly timing the delivery of pace pulses, the heart can be induced to contract in a coordinated rhythm, greatly improving its efficiency as a pump. Such devices are often used to treat patient's hearts exhibiting arrhythmias. Implanted rhythm management devices are also used to deliver high-energy defibrillation pulses via a lead wire having one or more electrodes disposed in or about the heart for providing defibrillation therapy.

Implanted rhythm management devices generally include sensing circuits to sense electrical signals from a heart tissue in contact with the electrodes. Then a controller in the implanted rhythm management device processes these signals and issues command signals to therapy circuits, for delivery of electrical energy such as pacing and/or defibrillation pulses to the appropriate electrodes in or about the heart to provide therapy to the heart. The controller may include a microprocessor or other controller for execution of software and/or firmware instructions. The software of the controller may be modified to provide different parameters, modes, and/or functions for the implantable device to adapt or improve performance of the device. Generally algorithms are used in software and/or firmware residing in the controller to discriminate between sensed coordinated and uncoordinated cardiac signals and to provide an appropriate therapy to the heart. Current techniques to discriminate cardiac rhythms in the sensed cardiac signals are based on interval information and ignore serial interval relationships in the sensed cardiac signals. Thus, a need exists for a more reliable, more sensitive method of discriminating cardiac rhythms in the sensed cardiac signals in implanted rhythm management devices to provide the appropriate therapy (whether to deliver pacing pulses or high-energy therapy) to the heart and to reduce patient morbidity and discomfort. Also, what is needed is an implanted rhythm management device that can save electrical energy and reduce patient discomfort by delivering high-energy defibrillation pulses only when lower energy therapies such as anti tachycardia pacing (low energy pacing) are not likely to restore normal function to the heart.

SUMMARY

The present invention provides, among other things, a technique for discriminating a coordinated cardiac rhythm from an uncoordinated cardiac rhythm using at least two sensed cardiac signals. The invention allows for reduced computation (when compared with morphology-based algorithms) and increased sensitivity and specificity in discriminating between coordinated and uncoordinated cardiac rhythms in the sensed cardiac signals. Also, the invention can reduce consumption of electrical energy stored in an implanted rhythm management device and increase longevity of the device by delivering high-energy defibrillation pulses only when essential, and by delivering low-energy electrical stimuli based on an improved rhythm stratification. Also, the invention can reduce patient discomfort by delivering high-energy defibrillation pulses only when low-energy therapies are not likely to restore normal function to the heart. It can also be envisioned that due to the reduction in energy consumption, the size of the implanted rhythm device can be reduced.

In one embodiment, at least two electrodes are disposed at two different locations in or around a heart to measure propagation time differences (interelectrode detection time differences) in cardiac complexes at the two different locations. This is accomplished by detecting times when the cardiac complexes associated with the at least two cardiac signals occur at the two different locations. A controller including an analyzer and a comparator receives the sensed cardiac complexes associated with the at least two cardiac signals through a sensing circuit. Then the analyzer computes a set of interelectrode detection time differences using the times when the sensed cardiac complexes associated with one of the at least two cardiac signals occurred and the corresponding times when the sensed cardiac complexes associated with the other of the at least two cardiac signals occurred for a predetermined time interval.

The analyzer further computes a detection time difference variability (detection time difference variability is a measure of consistency between computed interelectrode detection time differences; it is also described mathematically as a measure of an average absolute value of first difference of interelectrode detection times) using the computed set of interelectrode detection time differences. In this embodiment, the comparator compares the computed detection time difference variability to a predetermined detection time difference variability threshold value. In another embodiment, the comparator compares the computed detection time difference variability to a predetermined detection time difference variability threshold value to discriminate whether the sensed cardiac signals have coordinated or uncoordinated cardiac rhythms. In another embodiment, the comparator further classifies the sensed at least two cardiac signals based on the outcome of the comparison to identify a cardiac arrhythmia. Then the comparator issues a command signal based on the outcome of the comparison. In some embodiments, a therapy circuit coupled to the comparator provides an appropriate therapy to the heart through the at least two electrodes disposed in or about the heart based on the outcome of the comparison. As a result of using such a sequence-based computation to calculate the interelectrode detection time differences, the system is generally capable of providing superior performance over existing algorithms in discriminating between coordinated and uncoordinated cardiac rhythms, which neglect any serial cycle length properties such as: the interelectrode time differences, and the detection time difference variability which incorporate serial interval relationships.

In some embodiments, the electrodes are disposed in or around a heart. In one embodiment, the electrode is disposed in or around an atrial region of a heart to detect one of the at least two cardiac signals. In another embodiment, the electrode is disposed in or around a ventricular region of the heart to sense one of the at least two cardiac signals. In another embodiment, a cardiac therapy includes providing pacing pulse electrical energy, when an uncoordinated cardiac rhythm is sensed by the controller. In another embodiment, the therapy includes providing high-energy defibrillation pulse electrical energy when atrial fibrillation (AF) is sensed by the controller. In another embodiment, the therapy includes activating an implanted or external device to administer a drug therapy. It can be envisioned that the electrodes can be disposed in and/or around different regions of a heart to measure interelectrode time differences. In another embodiment, an external programmer, remote from an implanted cardiac rhythm management system, is used to communicate with the controller and to program the controller. In one embodiment, a timer is included to introduce a delay between receiving the command signal from the comparator and administering the drug therapy to the heart.

These and other aspects and advantages of the invention will become apparent from the following detailed description of the invention and viewing the drawings that form a part thereof.

DETAILED DESCRIPTION

Figure 1:
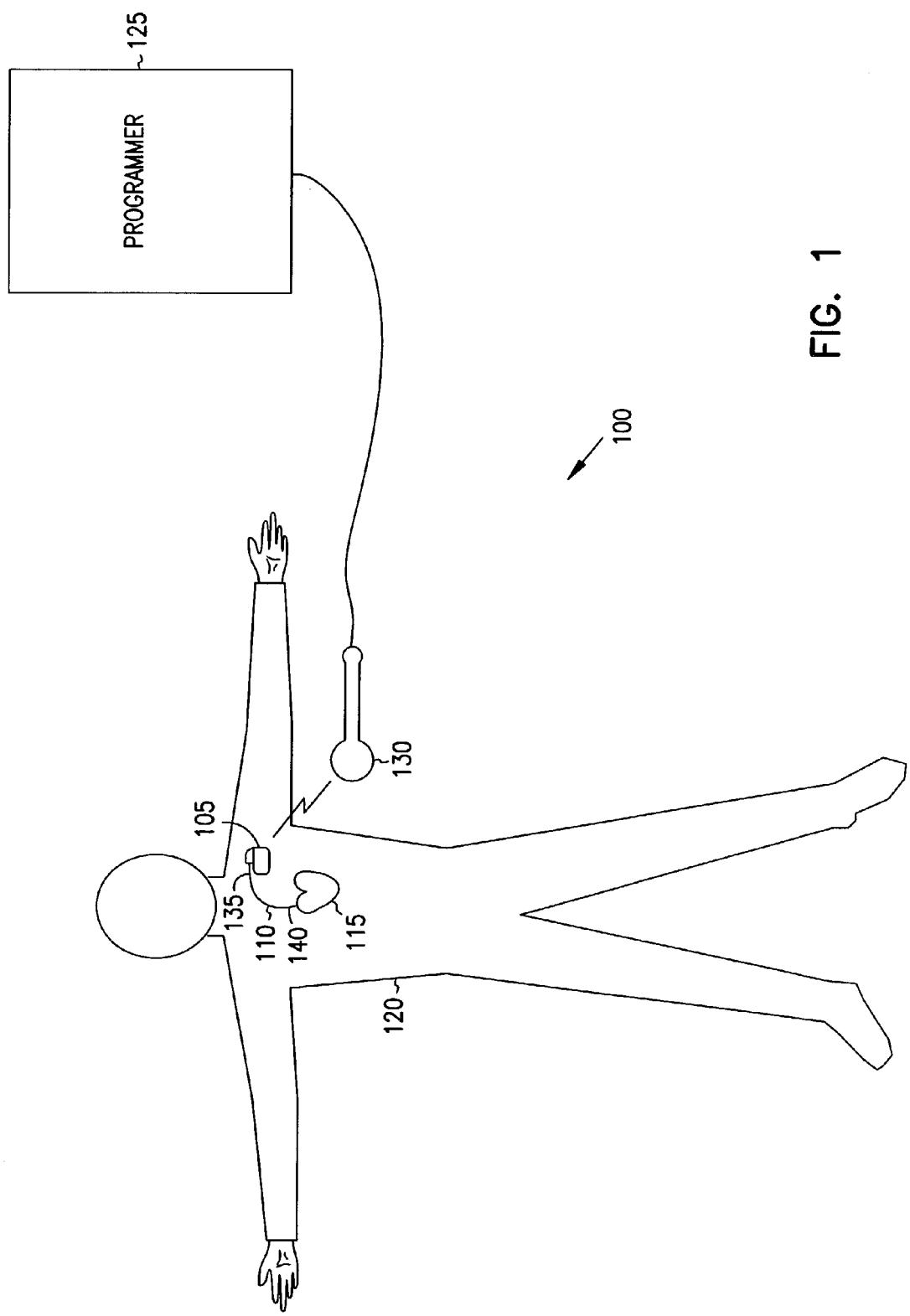
FIG. 1 is a schematic/block diagram illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

When functioning properly, the human heart maintains its own intrinsic rhythm, and is capable of pumping adequate blood throughout the body's circulatory system. The body's autonomic nervous system regulates intrinsic electrical heart activity signals that are conducted to atrial and ventricular heart chambers on the left and right sides of the heart. The electrical heart activity signals trigger resulting heart contractions that pump blood. However, some people can experience irregular and uncoordinated cardiac rhythms, referred to as arrhythmias. Some of the most common arrhythmias are atrial fibrillation (AF) and atrial flutter (AFL). Atrial fibrillation can result in significant patient discomfort and even death because of a number of associated problems, including: (1) an irregular heart rate which causes patient discomfort and anxiety, (2) loss of synchronous atrioventricular contractions which interferes with cardiac hemodynamics, resulting in varying levels of congestive heart failure, and (3) stasis of blood flow, which increases the vulnerability to thromboembolism.

One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such a system may be implanted in a patient to deliver therapy to the heart.

Cardiac rhythm management systems include, among other things, implanted rhythm management devices. Implanted rhythm management devices deliver, among other things, timed sequences of low-energy electrical stimuli, called pace pulses, to the heart, such as via a transvenous lead wire or catheter (referred to as a "lead") having one or more electrodes disposed in or about the heart. Coordinated heart contractions can be initiated in response to such pace pulses (this is referred to as "capturing" the paced heart). By properly timing the delivery of pace pulses, the heart can be induced to contract in a coordinated rhythm, greatly improving its efficiency as a pump. Such devices are often used to treat patient's hearts exhibiting arrhythmias. Implanted rhythm management devices are also used to deliver high-energy defibrillation pulses via a lead wire having one or more electrodes disposed in or about the heart for providing defibrillation therapy.

Implanted rhythm management devices generally include sensing circuits to sense electrical signals from a heart tissue in contact with the electrodes. Then a controller in the implanted rhythm management device processes these signals and issues command signals to therapy circuits, for delivery of electrical energy such as pacing and/or defibrillation pulses to the appropriate electrodes in or about the heart to provide therapy to the heart. The controller may include a microprocessor or other controller for execution of software and/or firmware instructions. The software of the controller may be modified to provide different parameters, modes, and/or functions for the implantable device to adapt or improve performance of the device. Generally algorithms are used in software and/or firmware residing in the controller to discriminate between sensed coordinated and uncoordinated cardiac signals and to provide an appropriate therapy to the heart. Current techniques to discriminate sensed cardiac signals are based on interval information and ignore serial interval relationships in the sensed cardiac signals. Thus, a need exists for a more reliable, more sensitive and less computationally oriented method of discriminating sensed cardiac signals in implanted rhythm management devices to provide the appropriate therapy (whether to deliver pacing pulses or high-energy therapy) to the heart and to reduce patient morbidity and discomfort. Also, what is needed is an implanted rhythm management device that can save electrical energy and reduce patient discomfort by delivering high-energy defibrillation pulses only when low energy pacing is not likely to restore normal function to the heart.

General System Overview

The present subject matter provides, among other things, a cardiac management system for discriminating coordinated and uncoordinated cardiac rhythm. The present system has an improved specificity in discriminating coordinated and uncoordinated cardiac rhythms due to an algorithm that uses serial interval relationships in sensed cardiac complexes between or among multiple locations in or around a heart. The system is also capable of providing a superior performance over existing algorithms. The present invention consists of a measure of variability in propagation time difference between corresponding cardiac complexes sensed by at least two electrodes located at different locations in or around a heart. Other aspects of the invention will be apparent on reading the following detailed description of the invention and viewing the drawings that form a part thereof.

Referring now to FIG. 1, there is one embodiment of a schematic/block diagram 100 illustrating portions of a cardiac rhythm management system and an environment in which it is used. In FIG. 1, system 100 includes an implantable cardiac rhythm management device 105, also referred to as an electronics unit, which is coupled by an intravascular endocardial lead 110, or other lead, to a heart 115 of a patient 120. System 100 also includes an external programmer 125 providing wireless communication with device 105 using a telemetry device 130. Catheter lead 110 includes a proximal end 135, which is coupled to a device 105, and a distal end 140, which is coupled to one or more portions of the heart 115.

Figure 2:
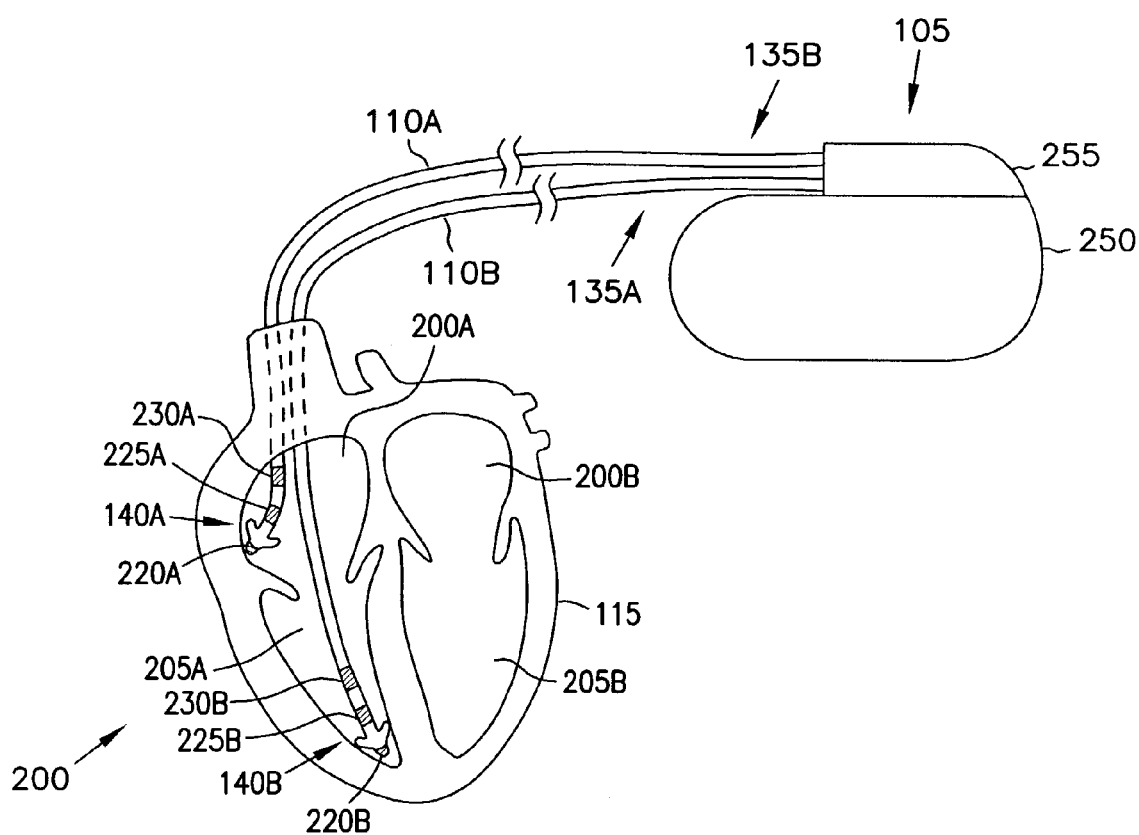
FIG. 2 is a schematic drawing illustrating generally one embodiment of portions of a cardiac rhythm management system coupled to a heart by a right atrial and a right ventricular electrode.

Referring now to FIG. 2, there is shown a schematic diagram 200 illustrating, by way of example, but not by way of limitation, one embodiment of an implantable rhythm management device 105 coupled by a right atrial lead 110A and a right ventricular lead 110B to a heart 115, which includes a right atrium 200A, a left atrium 200B, a right ventricle 205A, and a left ventricle 205B. In this embodiment, the lead 110A includes electrodes (electrical contacts) disposed in, around, or near a right atrium 200A of the heart 115, such as a ring electrode 225A and tip electrode 220A, for sensing signals and/or delivering therapy to the heart's right atrium 200A. Also in this embodiment, the lead 110B includes electrodes disposed in, around, or near a right ventricle 205A of the heart 115, such as a ring electrode 225B and tip electrode 220B, for sensing signals and/or delivering therapy to the heart's right ventricle 205A. Leads 110A and B optionally also includes additional electrodes, such as for delivering atrial and/or ventricular cardioversion/defibrillation and/or pacing therapy to the heart 115. Device 105 includes components that are enclosed in a hermetically sealed can 250. Additional electrodes may be located on the can 250, or on an insulating header 255, or on other portions of device 105, for providing unipolar pacing and/or defibrillation energy in conjunction with the electrodes disposed in or around the heart 115.

Figure 3:
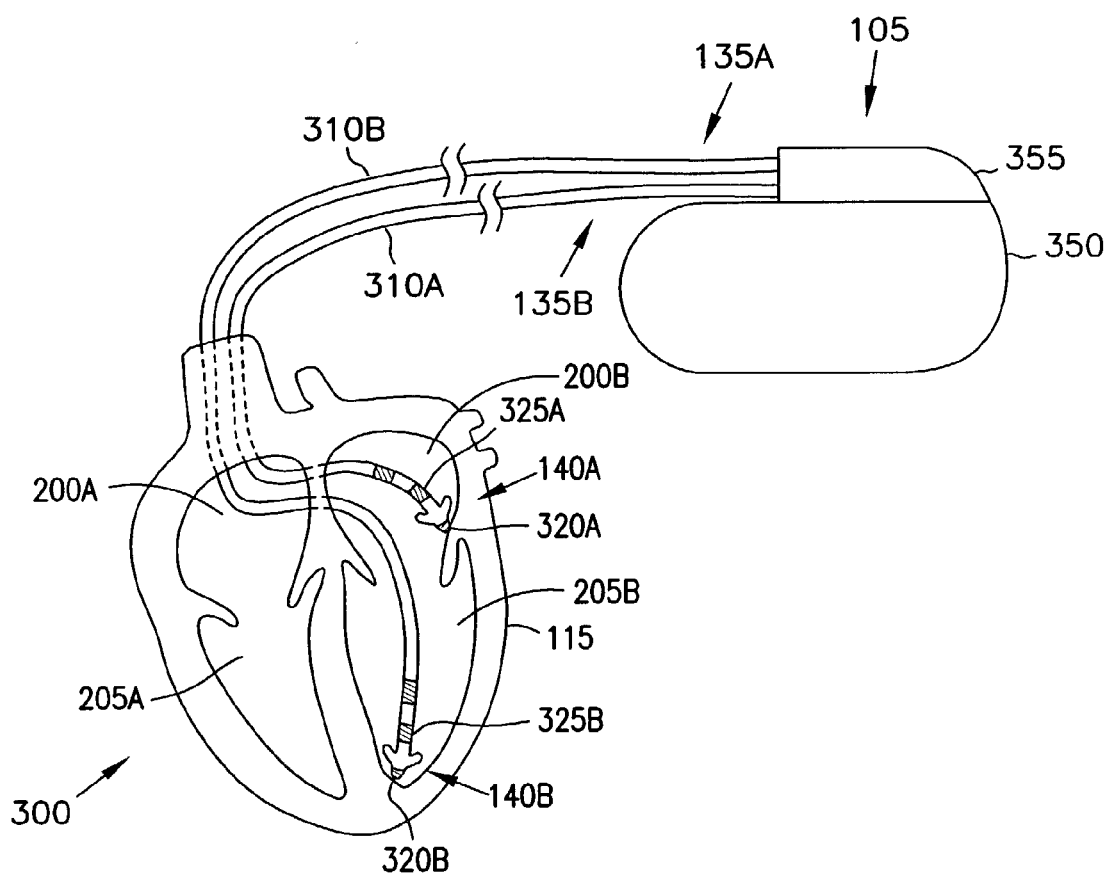
FIG. 3 is a schematic drawing illustrating generally one embodiment of portions of a cardiac rhythm management system coupled to the heart by a left atrial and a left ventricular electrode.

Referring now to FIG. 3, there is shown a schematic diagram 300 illustrating, by way of example, but not by way of limitation, one embodiment of an implantable rhythm management device 105 coupled by a left atrial lead 310A and a left ventricular lead 310B to a heart 115, which includes a right atrium 200A, a left atrium 200B, a right ventricle 205A, and a left ventricle 205B. In this embodiment, the lead 310A includes electrodes (electrical contacts) disposed in, around, or near a left atrium 200B of the heart 115, such as a ring electrode 325A and tip electrode 320A, for sensing signals and/or delivering therapy to the heart's left atrium 200B. Also in this embodiment, the lead 310B includes electrodes disposed in, around, or near a left ventricle 205B of the heart 115, such as a ring electrode 325B and tip electrode 320B, for sensing signals and/or delivering therapy to the heart's left ventricle 205B. Leads 310A and B optionally also includes additional electrodes, such as for delivering atrial and/or ventricular cardioversion/defibrillation and/or pacing therapy to the heart 115. Device 105 includes components that are enclosed in a hermetically sealed can 350. Additional electrodes may be located on the can 350, or on an insulating header 355, or on other portions of device 105, for providing unipolar pacing and/or defibrillation energy in conjunction with the electrodes disposed in or around the heart 115.

EXAMPLE CARDIAC RHYTHM MANAGEMENT DEVICE

Figure 4:
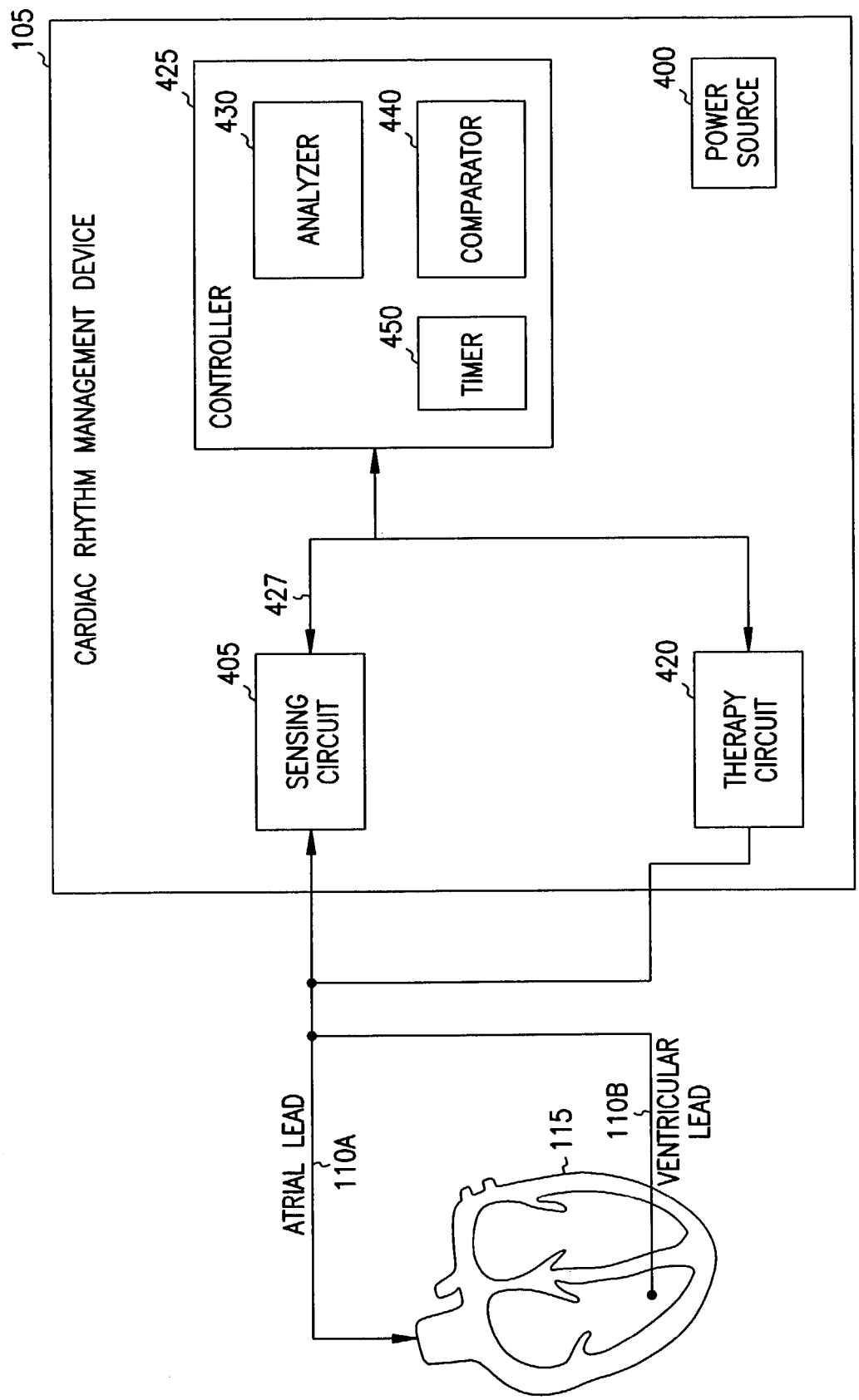
FIG. 4 is a schematic/block diagram illustrating generally one embodiment of portions of a cardiac rhythm management system showing interconnections between major functional components of the present invention and a heart.

FIG. 4 is a schematic diagram illustrating generally, by way of example, but not by way of limitation, one embodiment of portions of cardiac rhythm management device 105, which is coupled to the heart 115. Device 105 includes a power source 400, a controller 425, a sensing circuit 405, a therapy circuit 420, and an atrial lead 110A and a ventricular lead 110B coupled to the heart 115.

Sensing circuit 405 is coupled by atrial lead 110A and ventricular lead 110B to the heart 115 for receiving, sensing, and or detecting electrical heart signals. Such heart signals include atrial activations (also referred to as depolarizations or P-waves) which correspond to atrial contractions, and ventricular activations which correspond to ventricular contractions. Such heart signals include coordinated and uncoordinated cardiac rhythms. Sensing circuit 405 provides at least two sensed cardiac signals to controller 425, via leads 110A and 110B. Such signals provided to the controller 425 indicate, among other things, the presence of a cardiac arrhythmia. In one embodiment, the signals indicate atrial fibrillation and atrial flutter. Controller 425 also controls the delivery of therapy provided by the therapy circuit 420 and/or other circuits, as discussed below.

Controller 425 includes various modules, which are implemented either in hardware or as one or more sequences of steps carried out on a microprocessor or other controller. Such modules are illustrated separately for conceptual clarity; it is understood that the various modules of controller 425 need not be separately embodied, but may be combined and/or otherwise implemented, such as in software/firmware.

In general terms, the sensing circuit 405 senses electrical signal from a heart tissue in contact with a catheter lead 110A or 110B to which the sensing circuit 405 is coupled. The sensed cardiac signal from the sensing circuit 405 is then received and processed by an analyzer 430 of a controller 425 based on an algorithm that uses a serial interval relationship in computing the at least two sensed cardiac signals of the heart 115 to discriminate cardiac arrhythmia. In one embodiment, the algorithm discriminates coordinated from uncoordinated cardiac rhythm. Based on the outcome of the analyzer 430, comparator 440 of the controller 425 issues a command signal. In one embodiment, the comparator 440 issues a command signal to the therapy circuit 420, to deliver electrical energy (e.g., pacing and/or defibrillation pulses) to the heart 115 through the leads 110A and B. Controller 425 may include a microprocessor or other controller for execution of software and/or firmware instruction. In one embodiment, the software of controller 425 may be modified (e.g., by remote external programmer 105) to provide different parameters, modes, and/or functions for the implantable device 105 or to adapt or to improve performance of device 105.

Also shown in this embodiment, is a timer 450 included in the controller 425 to introduce a time delay between the command signal issued by the controller 425 and the therapy provided to the heart 115 by the therapy circuit 420. In one embodiment, the time delay is introduced (before administering a therapy) to ensure that the command signal issued by the controller is indeed based on a sustained detection of AF from AFL and not based on a spontaneous detection of AF from AFL. In another embodiment the predetermined delay can be introduced during a ventricular repolarization to avoid inducing a ventricular therapy. In one embodiment, the predetermined time delay is approximately in the range of 1 second to 180 seconds.

In operation, the sensing circuit 405 receives sensed complexes associated with at least two cardiac signals from at least two electrodes disposed at different locations in or around the heart 115. Then the analyzer 430 receives the sensed complexes associated with the at least two cardiac signals and computes a set of interelectrode detection time differences (propagation between two locations of the heart 115) between the sensed cardiac complexes associated with one of the at least two cardiac signals and the corresponding cardiac complexes associated with the other of the at least two cardiac signals for a predetermined time interval.

Figure 5A:
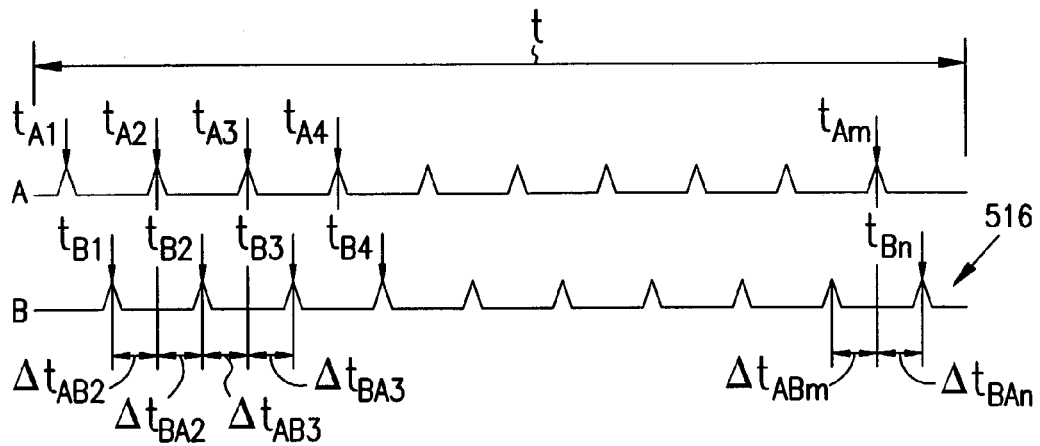
FIG. 5A is a timing diagram illustrating generally one embodiment of normal sinus rhythms sensed at two locations within a heart for a predetermined time interval 't'.

FIG. 5A shows a timing diagram of one embodiment of a normal sinus rhythm (cardiac signals) A and B sensed from right and left chambers of the heart 115 respectively, for a given interval of time t by the sensing circuit 405. Shown in FIG. 5A are M sensed cardiac complexes associated with the right atrium cardiac signal, and N sensed complexes associated with the left atrium cardiac signal for the given interval t. It should be noted that m and n (m is an index ranging from 0 to M−1; and similarly, n is an index ranging from 0 to N−1) are generally not equal and are not constrained to increment at the same rate. In this example embodiment, the analyzer 430 computes a first set of interelectrode detection time differences $\Delta_{tAB2}$, $\Delta_{tAB3}$, ... $\Delta_{tABm}$ using the sensed cardiac complexes associated with the right atrium cardiac signal A and the corresponding cardiac complexes associated with the left atrium cardiac signal B. The time difference $\Delta_{tAB2}$ is a time computed between time $t_{A2}$ when a sensed first complex associated with the right atrium cardiac signal A occurs and a time $t_{B1}$ when the corresponding sensed first complex associated with the left atrium cardiac signal B occurs (it is the time difference between sensed complex at $t_{A2}$ with respect to the sensed complex at $t_{B1}$), $\Delta_{tAB3}$ is a time difference computed between time $t_{A3}$ when a sensed second complex associated with the right atrium cardiac signal A occurs and a time $t_{B2}$ when the corresponding left atrium sensed second complex associated with the cardiac signal B occurs, and $\Delta_{tABm}$ is a time difference computed between time $t_{Am}$ when an mth complex associated with the right atrium cardiac signal A occurs and a time $t_{Bn}$ when the corresponding nth complex associated with the left atrium cardiac signal B occurs (this is a detection that occurs before $t_{Am}$), and so on.

Then the analyzer 430 computes a first detection time difference variability using the computed first set of interelectrode detection time differences and compares the computed first detection time difference variability to a predetermined detection time difference variability threshold value and issues a command signal based on the outcome of the comparison. In the embodiment shown in FIG. 4A, generally a computed detection time difference variability will be very low, because the cardiac complexes are generally coordinated in a normal sinus rhythm and the time differences between sensed cardiac complexes associated with cardiac signal A and corresponding sensed cardiac complexes associated with cardiac signal B are generally consistent.

In another embodiment, the analyzer 430 further computes a second set of interelectrode detection time differences $\Delta_{tBA2}$, $\Delta_{tBA3}$, ... $\Delta_{tBAn}$. Where the time difference $\Delta_{tBA2}$ is a time between sensing a first complex $t_{B2}$ associated with the cardiac signal B and sensing the corresponding first complex $t_{A2}$ associated with the cardiac signal A (it is the difference between the time $t_{B2}$ of the sensed complex of cardiac signal B and time $t_{A2}$ of the corresponding sensed complex of cardiac signal A), $\Delta_{tBA3}$ is a time between sensing a second complex at $t_{B3}$ associated with the cardiac signal B and sensing the corresponding second complex at $t_{A3}$ associated with the cardiac signal A, and $\Delta_{tBAn}$ is a time between sensing an nth complex at $t_{Bn}$ associated with the cardiac signal B and sensing the corresponding mth complex at $t_{Am}$ associated with the cardiac signal A and so on.

Then the analyzer 430 computes a second detection time difference variability from the computed second set of interelectrode detection time differences. In one embodiment, the analyzer 430 computes the first and second detection time difference variabilities using $$S_{AB} = \frac{1}{M-1} \sum_{m=1}^{M-1} |\Delta t_{AB}[m] - \Delta t_{AB}[m-1]| \text{ and}$$

$$S_{BA} = \frac{1}{N-1} \sum_{n=1}^{N-1} |\Delta t_{BA}[n] - \Delta t_{BA}[n-1]|$$

where $S_{AB}$ and $S_{BA}$ are first and second detection time difference variabilities, M is a total number of activations sensed at site A within a predetermined time interval t, and N is a total number of activations sensed at site B within the predetermined time interval 't'. In this example embodiment, M and N are not equal and not constrained to increment at a same rate.

Then the comparator 440 compares the computed second detection time difference variability to the predetermined detection time difference variability threshold value and issues a command signal based on the outcome of the comparison. In some embodiments, the comparator 440 compares the computed first and second detection time difference variabilities to the predetermined detection time difference variability threshold value and issues a command signal based on the outcome of the comparison. In the example embodiment, shown in FIG. 5A, the sensed cardiac signals A and B have normal sinus rhythms. Also in this example embodiment, the computed first and second detection time difference variabilities are generally the same because in normal sinus rhythms, such as the one shown in FIG. 5A, generally the cardiac complexes are coordinated and the detection time difference variability between cardiac complexes is generally insignificant. In this example embodiment, the controller 425 would classify the sensed cardiac signals A and B as coordinated cardiac rhythms and would not be delivering a therapy to the heart 115.

Figure 5B:
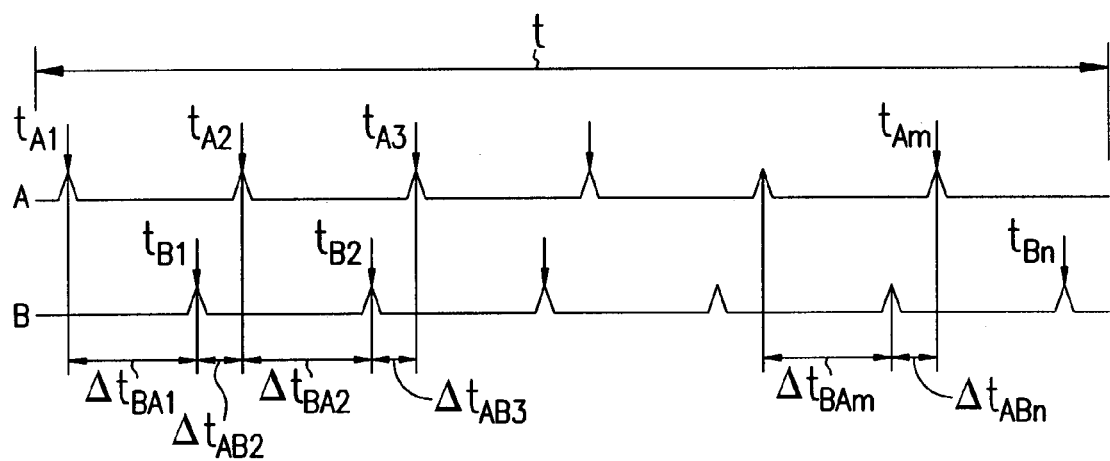
FIG. 5B is a timing diagram illustrating generally one embodiment of determining atrial flutter from the sensed cardiac signals according to the teachings of the present subject matter.

FIG. 5B shows a timing diagram of one embodiment of cardiac signals A and B sensed from a right atrium and a left atrium respectively, of a heart experiencing atrial flutter for a given interval of time t by the sensing circuit 405. Further, FIG. 5B illustrates the use of the present subject matter to diagnose a heart experiencing atrial flutter. In this example embodiment, the sensed cardiac signals A and B are still coordinated (similar to the cardiac signals shown in FIG. 5A), except that the sensed cardiac signals shown in FIG. 5B have a longer time between cardiac complexes associated with cardiac signal A and corresponding cardiac complexes associated with cardiac signal B due to the heart experiencing an atrial flutter. In this embodiment, the analyzer 430 would classify the sensed cardiac signals A and B as atrial flutter because the sensed cardiac signals A and B have a substantially higher detection time difference variability when compared to a predetermined detection time difference variability threshold value even though the cardiac complexes in the sensed cardiac signals A and B are coordinated.

In some embodiments, the analyzer 430 further computes an average time difference for the given interval of time t using $$\bar{I}_{AB} = \frac{1}{M} \sum_{m=0}^{M-1} \Delta t_{AB}[m] \text{ and } \bar{I}_{BA} = \frac{1}{N} \sum_{n=0}^{N-1} \Delta t_{BA}[n]$$

where $I_{AB}$ and $I_{BA}$ are average time differences associated with the corresponding computed first and second interelectrode time differences. Then the analyzer 430 further compares both the computed detection time difference variabilities and determines a minimum detection time difference variability. In the example embodiment, shown in FIG. 5A, the minimum detection time difference variability will be $S_{BA}$. Then the analyzer 430 discriminates the sensed cardiac signals by comparing the determined minimum detection time difference variability $S_{BA}$ to the predetermined detection time difference variability threshold value. This process of comparing the minimum detection time difference variability assures a conservative approach in discriminating the sensed at least two cardiac signals, and also by using the minimum detection time difference variability to compare, the process is normalizing to capture only cardiac signals having substantially higher detection time difference variability when compared with the computed average time difference.

Figure 5C:
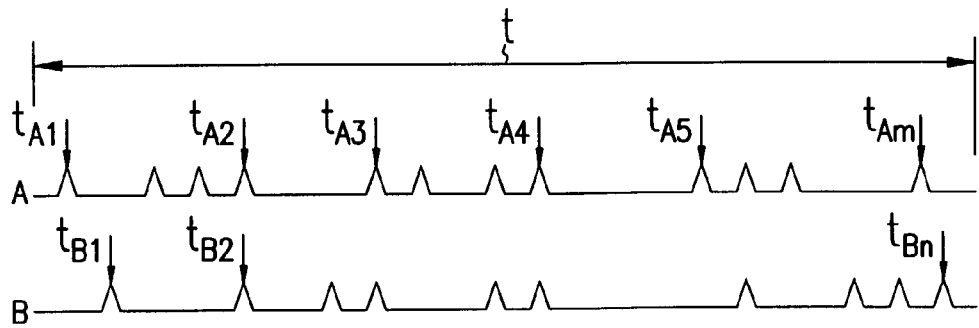
FIG. 5C is a timing diagram illustrating generally one embodiment of determining atrial fibrillation from the sensed cardiac signals according to the teachings of the present subject matter.

FIG. 5C shows a timing diagram of one embodiment of cardiac signals A and B sensed from a right atrium and a left atrium of a heart experiencing atrial fibrillation for a given interval of time t by the sensing circuit 405. FIG. 5C also illustrates the use of the present invention to diagnose a heart experiencing atrial fibrillation. In this example embodiment, the detection time difference variability between the cardiac complexes associated with cardiac signal A and corresponding cardiac complexes associated with cardiac signal B are substantially different and highly variable. Also in this example embodiment, the time differences between the cardiac complexes associated with cardiac signal B and corresponding cardiac complexes associated with cardiac signal A are substantially different and highly variable. In addition, the computed first and second detection time difference variabilities would be substantially different (first detection time difference variability is computed based on interelectrode detection time differences and second detection time difference variability is computed based on interelectrode detection time differences). In this example embodiment, the analyzer 430 would classify the sensed cardiac signals A and B as atrial fibrillation because of a substantially high detection time difference variability in interelectrode detection time differences, and also because both the computed first and second detection time difference variabilities would be substantially different when compared with the predetermined detection time difference variability threshold value. Further, in this embodiment if only one of the computed first and second detection time difference variabilities is different, the analyzer 430, would not classify the sensed right atrial and left atrium cardiac signals A and B as having atrial fibrillation, and hence would not deliver a therapy to the heart 115. Similarly, the present subject matter can also be used to diagnose ventricular tachycardia, ventricular fibrillation, interventricular differences, and for other organized rhythms, and to provide an appropriate therapy to the heart 115.

Figure 6:
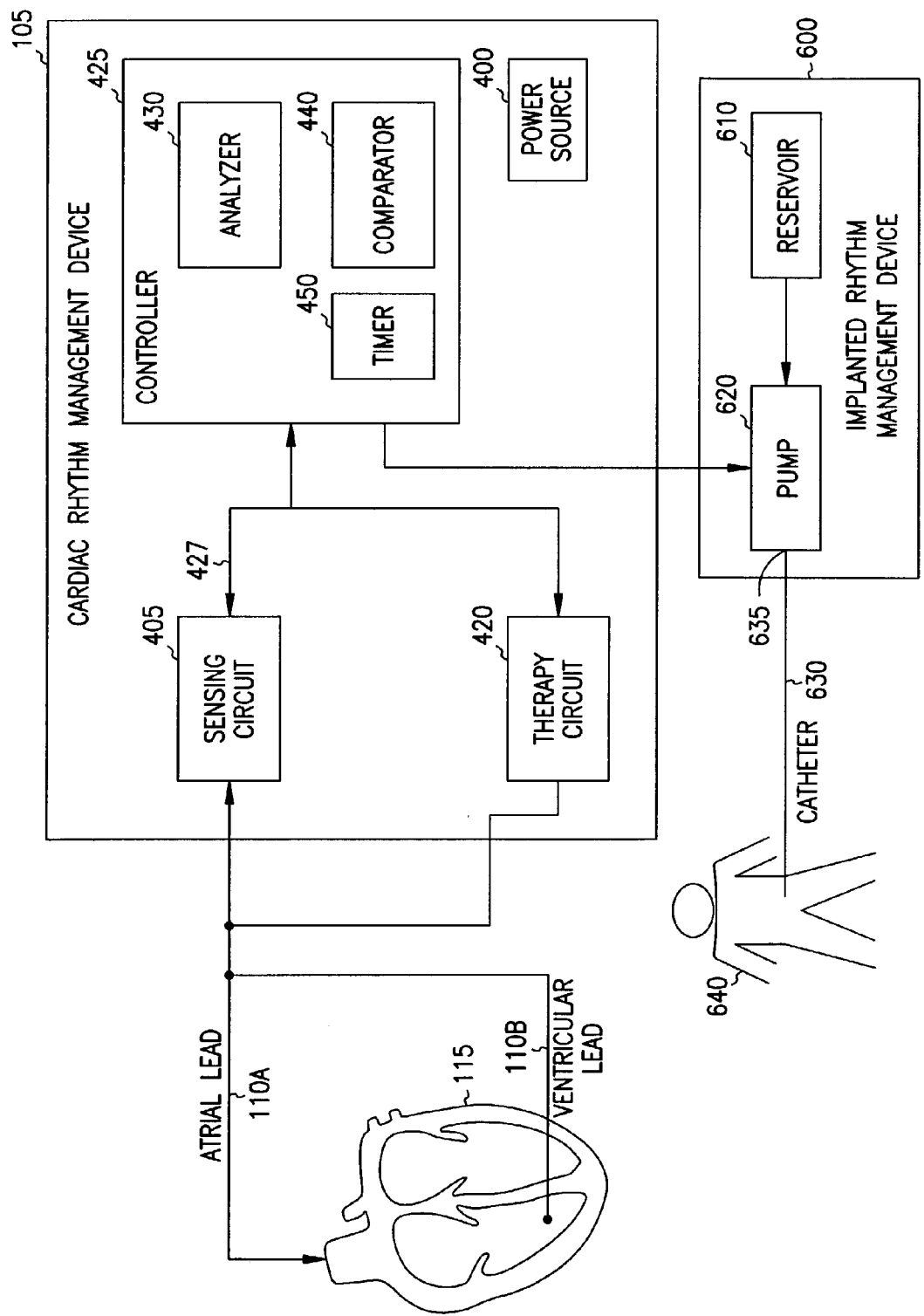
FIG. 6 is a schematic/block diagram illustrating one embodiment of interconnecting an implanted rhythm management device in addition to what is shown in FIG. 4.

FIG. 6, is a schematic drawing, similar to FIG. 4, illustrating generally, by way of example, but not by way of limitation, one embodiment of an implanted rhythm management device 600, coupled to the cardiac rhythm management device 105. The implanted rhythm management device 600 includes a reservoir 610 to hold a drug, and a pump 620 coupled to the reservoir 610, and a catheter 630 coupled to the pump on end 635 and disposed inside a patient's body on the other end 640, administers the drug to the patient's body upon receiving a command signal from the controller 425. In one embodiment, the timer 450 introduces a predetermined delay for administering the drug upon receiving the command signal from the comparator 440. In one embodiment, the predetermined delay is approximately in the range of about 1 second to 180 seconds. In one embodiment, the implanted rhythm management device 600 and the cardiac rhythm management device 425 are integrated into a single implantable unit.

Figure 7:
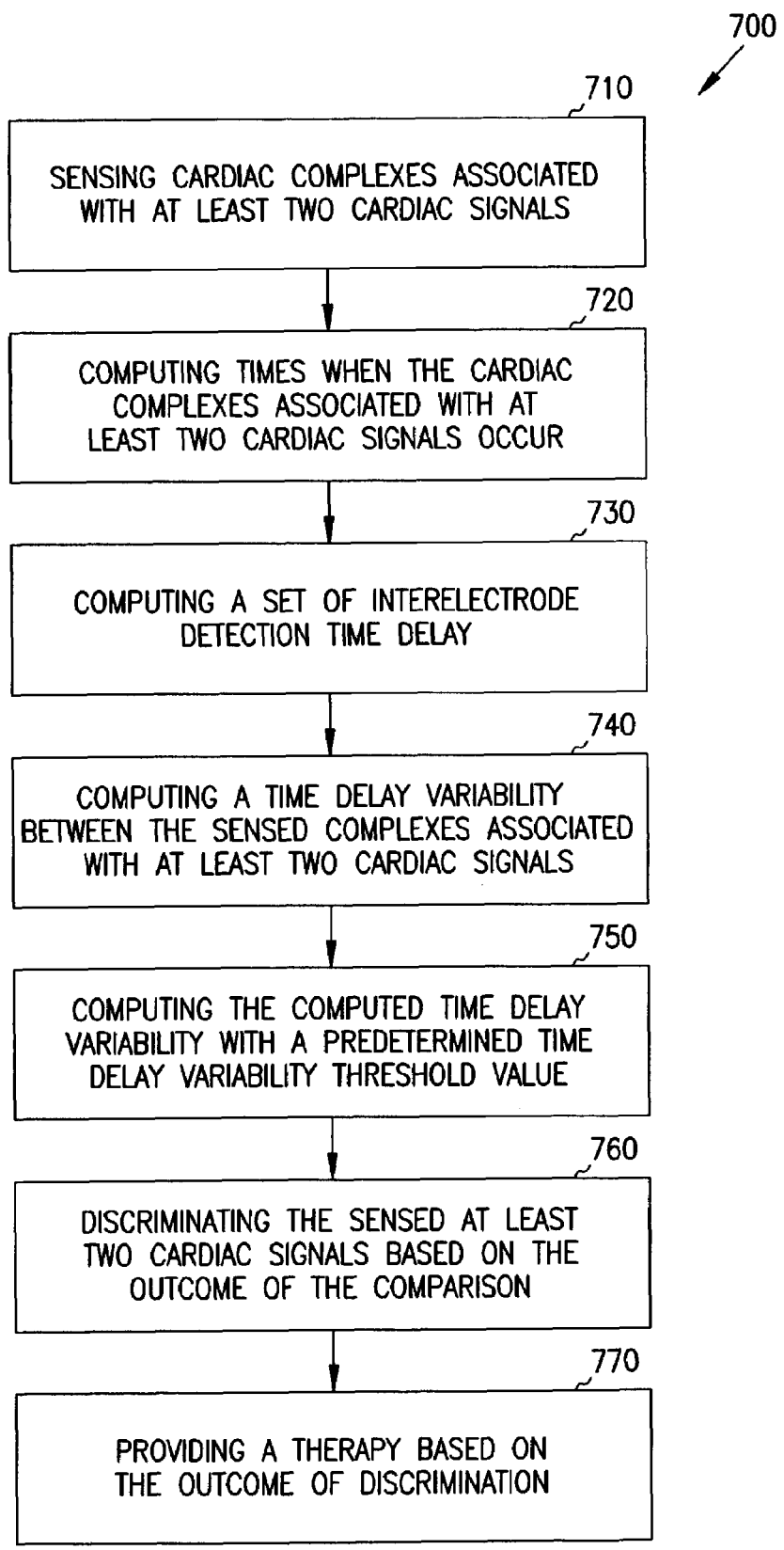
FIG. 7 is flow diagram illustrating generally one embodiment of operation of the cardiac rhythm management device according to the teachings of the present invention.

Referring now to FIG. 7, there is shown one embodiment of a method 700 of discriminating cardiac rhythms according to the teachings of the present subject matter. At 710, the method requires sensing cardiac signals from at least two different locations of a heart. In some embodiments, this is accomplished by disposing the at least two electrodes in or around a heart to sense the at least two cardiac signals.

At 720, the method 700 requires computing times when the cardiac complexes associated with the sensed at least two cardiac signals occurs. Additionally, at 730 the method 700 requires computing a set of interelectrode detection time differences from the computed times when the cardiac complexes associated with the sensed at least two cardiac signals occurs. The method of computing the set of interelectrode detection time differences are described in detail in FIGS. 5A, 5B & 5C. Further, at 740 the method 700 requires computing a detection time difference variability using the computed set of interelectrode detection time differences as described in detail in FIG. 5A.

At 750, the method 700 requires comparing the computed detection time difference variability with a predetermined detection time difference variability threshold value. Then, at 760 the method 700 discriminates the sensed at least two cardiac signals based on the outcome of the comparison performed at 750. In some embodiments, the method 700 discriminates an atrial fibrillation from an atrial flutter. In some other embodiments, the method 700 discriminates a ventricular fibrillation from a ventricular tachycardia. At 770, the method 700 can provide a therapy to a heart based on the outcome of the discrimination.

CONCLUSION

The above-described system provides, among other things, a cardiac rhythm management system to discriminate coordinated from uncoordinated cardiac signals by computing propagation differences in the sensed cardiac complexes associated with at least two cardiac signals. The present technique has an increased sensitivity and specificity in discriminating between coordinated and uncoordinated cardiac signals over the current techniques.

This application is intended to cover any adaptations or variations of the present invention. It is manifestly intended that this invention be limited only by the claims and equivalents thereof.

What is claimed is:

1. A system adapted to be coupled to a heart having a first location and a second location, comprising:

at least two electrodes to sense a first cardiac signal from the first location and a second cardiac signal from the second location, the first and second signals associated with cardiac complexes;

a signal sensing circuit, coupled to the at least two electrodes to receive and amplify the cardiac complexes;

a controller, coupled to the signal sensing circuit, wherein the controller receives the amplified cardiac complexes, and wherein the controller comprises:

an analyzer to compute a set of interelectrode detection time differences each between one of the cardiac complexes associated with the first location and the one of the cardiac complexes associated with the second location for a predetermined time interval, wherein the interelectrode detection time differences are each a propagation time of one of the cardiac complexes from the first location to the second location;

wherein the analyzer further computes a detection time difference variability using the computed set of interelectrode detection time differences, wherein the detection time difference variability includes a measure of an average absolute value of the interelectrode detection time differences; and a comparator, coupled to the analyzer, to compare the computed detection time difference variability with a predetermined detection time difference variability threshold value, classify the first and second signals based on the outcome of the comparison and issue a command signal based on the classification.

2. The system of claim 1, further comprises:

a therapy circuit coupled to the comparator, to deliver a high-energy electrical therapy through one of the at least two electrodes upon receiving the command signal from the comparator.

3. The system of claim 1, where the at least two electrodes are first and second electrodes.

4. The system of claim 3, wherein the first and second cardiac signals are associated with the first and second electrodes, respectively.

5. The system of claim 4, where the analyzer computes the set of interelectrode detection time differences between the sensing of the cardiac complexes associated with the first location and the sensing of the corresponding cardiac complexes associated with the second location, and the analyzer further computes a second set of interelectrode detection time differences between the sensing of the cardiac complexes associated with the second location and the sensing of the corresponding cardiac complexes associated with the first location.

6. The system of claim 5, where the analyzer further computes a first detection time difference variability and a second detection time difference variability using the computed first and second set of interelectrode detection time differences, respectively.

7. The system of claim 6, where the comparator compares the computed first and second detection time difference variabilities with a predetermined detection time difference variability threshold value, and issues a command signal based on the outcome of the comparison.

8. The system of claim 7, where the comparator further classifies the sensed first and second cardiac signals based on the outcome of the comparison to identify a cardiac arrhythmia.

9. The system of claim 7, where the comparator further classifies the sensed first and second cardiac signals based on the outcome of the comparison to identify an atrial fibrillation from an atrial flutter.

10. The system of claim 7, where the comparator further classifies the sensed first and second cardiac signals based on the outcome of the comparison to identify a ventricular fibrillation from a ventricular tachycardia.

11. The system of claim 7, in which the controller further comprises:
a timer coupled to the comparator, to provide a predetermined variable delay in an electrical energy delivered through at least one of the at least two electrodes.

12. The system of claim 11, where the electrical energy is a pacing pulse electrical energy.

13. The system of claim 11, where the electrical energy is a defibrillation pulse electrical energy.

14. The system of claim 1, further comprising:
an implantable rhythm management device.

15. The system of claim 14, where the implanted rhythm management device further comprises:
a reservoir to hold a drug;
a pump coupled to the reservoir; and
a catheter, having a first end and a second end, where the first end is coupled to the pump, and the second end is adapted to deliver a drug therapy to one or more regions of a patient's body, wherein the device administers the drug to the patient through the catheter upon receiving the command signal.

16. The system of claim 15, where the controller further comprises:
a timer, where the timer is coupled to the comparator and provides a predetermined time delay to administer the drug upon receiving the command signal from the comparator.

17. The system of claim 16, in which the predetermined time delay is approximately in the range of 1 second to 180 seconds.

18. The system of claim 1, wherein one of the first and second cardiac signals is an atrial signal.

19. The system of claim 1, wherein one of the first and second cardiac signals is a ventricular signal.

20. The system of claim 1, where the system comprises a cardiac rhythm management system.

21. The system of claim 1, where the predetermined time interval 't' includes 'N' number of cardiac complexes sensed by one of the at least two electrodes.

22. The system of claim 21, where the 'N' number of cardiac complexes are approximately in a range of about ten (10) to fifteen (15) cardiac complexes.

23. A controller to discriminate between coordinated and uncoordinated cardiac rhythms from sensed cardiac complexes associated with at least two cardiac signals sensed at two different locations of a heart having a first location and a second location, the controller comprising:
an analyzer, to compute a set of interelectrode detection time differences each between a sensed time when the one of the cardiac complexes associated with the first location occurs and a sensed time when the one of the cardiac complexes associated with the second location occurs for a predetermined time interval, wherein the interelectrode detection time differences are each a propagation time of the one of the cardiac complexes occurring from the first location to the second location, wherein the analyzer further computes a detection time difference variability in the computed set of interelectrode detection time differences, and wherein the detection time difference variability includes a measure of an average absolute value of the interelectrode detection time differences; and
a comparator, coupled to the analyzer, to compare the computed detection time difference variability with a predetermined detection time difference variability threshold value, classify the first and second signals based on the outcome of the comparison and issue a command signal based on the classification.

24. The controller of claim 23, where the comparator further classifies the sensed at least two cardiac signals to identify a cardiac arrhythmia based on the outcome of the comparison.

25. The controller of claim 24, where the comparator further classifies the sensed at least two cardiac signals based on the outcome of the comparison to identify an atrial fibrillation from an atrial flutter.

26. The controller of claim 24, where the comparator further classifies the sensed at least two cardiac signals based on the outcome of the comparison to identify a ventricular fibrillation from a ventricular tachycardia.

27. A method comprising:
computing interelectrode detection time differences from sensed cardiac complexes associated with at least two cardiac signals sensed at first and second locations in a heart, wherein the interelectrode detection time differences are each a propagation time of one of the sensed cardiac complexes from the first location to the second location;
computing a detection time difference variability from the computed interelectrode detection time differences, wherein the detection time difference variability includes a measure of an average absolute value of the interelectrode detection time differences; and
classifying the sensed at least two cardiac signals by comparing the computed detection time difference variability with a predetermined detection time difference variability threshold value.

28. The method of claim 27, wherein computing the interelectrode time differences further comprises:
computing a set of interelectrode detection time differences between the computed times when cardiac complexes associated with one of the at least two cardiac signals occur and the corresponding computed times when the cardiac complexes associated with the other of the at least two cardiac signals occur for a predetermined time interval.

29. The method of claim 28, further comprising:
discriminating a cardiac arrhythmia based on the outcome of the comparison.

30. The method of claim 29, where discriminating the cardiac arrhythmia further comprises:
discriminating an atrial fibrillation from an atrial flutter.

31. The method of claim 29, where discriminating the cardiac arrhythmia further comprises:
discriminating a ventricular fibrillation from a ventricular tachycardia.

32. The method of claim 29, wherein sensing the cardiac complexes associated with the at least two cardiac signals comprises:
sensing cardiac complexes associated with first and second cardiac signals.

33. The method of claim 32, wherein computing the times when the cardiac complexes associated with the sensed first and second cardiac signals comprises:
  computing the times when the cardiac complexes associated with the first cardiac signal occur; and
  computing the times when the corresponding cardiac complexes associated with the second cardiac signal occur.

34. The method of claim 33, where discriminating the cardiac arrhythmia further comprises:
  computing a first set of interelectrode detection time differences between the sensed cardiac complexes associated with the first cardiac signal and the corresponding sensed cardiac complexes associated with the second cardiac signal, respectively;
  computing a first detection time difference variability using the computed first set of interelectrode detection time differences;
  computing a second set of interelectrode detection time differences between the sensed cardiac complexes associated with the second cardiac signal and the corresponding sensed cardiac complexes associated with the first cardiac signal, respectively;
  computing a second detection time difference variability using the computed second set of interelectrode detection time differences;
  comparing the computed first and second detection time difference variabilities to a predetermined detection time difference variability threshold value; and
  issuing a command signal based on the outcome of the comparison.

35. The method of claim 34, further comprises:
  discriminating the sensed first and second cardiac signals based on the outcome of the comparison.

36. The method of claim 34, where discriminating the first and second cardiac signals further comprises:
  classifying the sensed first and second cardiac signals as coordinated cardiac rhythm or as an uncoordinated cardiac rhythm based on the outcome of the comparison.

37. The method of claim 34, further comprises:
  providing a high-energy therapy to a heart through at least one of the at least two electrodes upon receiving the command signal.

38. The method of claim 34, further comprises:
  providing a cardiac therapy to a heart upon receiving the command signal.

39. The method of claim 34, further comprises:
  activating an implanted device to administer a drug therapy to the heart upon receiving the command signal.

40. The method of claim 34, where sensing the first and second cardiac signals comprises sensing atrial signals.

41. The method of claim 34, where sensing the first and second cardiac signals comprise sensing ventricular signals.

42. The method of claim 34, where the predetermined time interval 't' includes 'N' number of cardiac complexes sensed by one of the at least two electrodes.

43. The method of claim 42, where the 'N' number of cardiac complexes is approximately in a range of about ten (10) to fifteen (15).

44. The method of claim 34, further comprises:
  computing a first and second average detection time difference using the corresponding computed first and second set of interelectrode detection time differences;
  comparing the computed first and second detection time difference variabilities to the corresponding computed first and second average detection time difference variabilities;
  determining a lower detection time difference variability based on the outcome of the comparison of the first and second detection time difference variabilities to reduce an effect of inflated detection time difference variability due to substantially longer cycle lengths introduced by a cardiac arrhythmia such as an atrial flutter;
  comparing the determined lower detection time difference variability with a predetermined detection time difference variability threshold value; and
  issuing a command signal based on the outcome of the comparison.

* * * * *

UNITED STATES PATENT AND TRADEMARK OFFICE
CERTIFICATE OF CORRECTION

PATENT NO.       : 7,369,890 B2
APPLICATION NO.  : 10/435487
DATED            : May 6, 2008
INVENTOR(S)      : Lovett Page 1 of 1

It is certified that error appears in the above-identified patent and that said Letters Patent is hereby corrected as shown below:

On Sheet 2 of 7, in Fig. 2, line 1, before "105" delete "135B".

On Sheet 2 of 7, in Fig. 2, line 3, after "110B" delete "135A".

On Sheet 2 of 7, in Fig. 2, line 5, above "225A" delete "230A".

On Sheet 2 of 7, in Fig. 2, line 7, above "220A" delete "140A".

On Sheet 2 of 7, in Fig. 2, line 10, above "225B" delete "230B".

On Sheet 2 of 7, in Fig. 2, line 12, above "220B" delete "140B".

On Sheet 3 of 7, in Fig. 3, line 1, before "105" delete "135A".

On Sheet 3 of 7, in Fig. 3, line 3, after "310A" delete "135B".

On Sheet 3 of 7, in Fig. 3, line 6, above "320A" delete "140A".

On Sheet 3 of 7, in Fig. 3, line 11, above "320B" delete "140B".

On Sheet 4 of 7, in Fig. 4, line 5, after "405" delete "427".

On Sheet 6 of 7, in Fig. 6, line 5, after "405" delete "427".

Signed and Sealed this

Twelfth Day of August, 2008

JON W. DUDAS
*Director of the United States Patent and Trademark Office*